US007615641B2

(12) United States Patent
Milanova

(10) Patent No.: US 7,615,641 B2
(45) Date of Patent: Nov. 10, 2009

(54) LONG CHAIN ALIPHATIC ALCOHOL DERIVATIVES AND METHODS OF MAKING AND USING SAME

(75) Inventor: Radka Milanova, Vancouver (CA)

(73) Assignee: Sino Pharmaceuticals Corporation, Richmond, BC (CA)

( * ) Notice: Subject to any disclaimer, the term of this patent is extended or adjusted under 35 U.S.C. 154(b) by 0 days.

(21) Appl. No.: 10/894,023

(22) Filed: Jul. 20, 2004

(65) Prior Publication Data

US 2006/0020135 A1     Jan. 26, 2006

(51) Int. Cl.
C07D 213/46    (2006.01)
C07D 213/24    (2006.01)
(52) U.S. Cl. ...................... 546/319; 546/318
(58) Field of Classification Search ............... 514/356, 514/315, 354; 546/318, 319, 326, 327, 245
See application file for complete search history.

(56) References Cited

U.S. PATENT DOCUMENTS

| 5,856,316 | A | 1/1999 | Laguna Granja et al. |
| 6,015,821 | A * | 1/2000 | Horrobin et al. ............ 514/355 |
| 6,197,832 | B1 | 3/2001 | Sorkin, Jr. |
| 6,328,998 | B1 | 12/2001 | Cavazza |
| 6,403,619 | B1 * | 6/2002 | Jacobson et al. ............ 514/356 |
| 6,500,451 | B2 | 12/2002 | Adams |
| 2002/0016314 | A1 | 2/2002 | Schersl |
| 2002/0192353 | A1 | 12/2002 | Cain et al. |

FOREIGN PATENT DOCUMENTS

| EP | 00519993 B1 | 6/1995 |
| EP | 01121928 A1 | 8/2001 |
| EP | 01249180 A2 | 10/2002 |
| EP | 1 161 884 B1 | 3/2003 |
| JP | 58017179 A2 | 2/1983 |
| JP | 61060893 A2 | 3/1986 |
| JP | 05044070 A2 | 2/1993 |
| JP | 2002 345414 A2 | 12/2002 |
| WO | WO 91/13931 | 3/1991 |
| ZA | 982744 | 4/1998 |

OTHER PUBLICATIONS

Palacin, S. et al.: Molecular Engineering: Highly ordered langmuir-biodgett films based on a cobalt phthalocyanine and its axial complexation. J. Phys. Chem., vol. 93, pp. 7195-7199, 1989.*
Oesch, U. et al.: Design of neutral hydrogen ion carriers for solvent polymeric membrane electrodes of selected pH range. Anal. Chem. vol. 58, pp. 2285-2289, 1986.*
Bertelsen et al., Structural Elucidation of Alkyl-Branched Chain Aliphatic Alcohols, Fette Seigen Anstrichmittel No. 9, pp. 336-342 (1985) Sweden.
Gamez et al., Dose-Dependent Cholesterol-Lowering Effects of D-003 on Normocholesterolemic Rabbits, Current Therapeutic Research, pp. 460-468, vol. 61, No. 7, (2000) Cuba.

Molina et al., Antiplatelet and Antithrombotic Effect of D-003, pp. 137-143, Pharmaceutical Research, vol. 42, No. 2, (2000) Cuba.
Taylor et al., Octacosanol in Human Health, Nutrition 19:192-195, (2003) USA.
Mdluli et al., Inhibition of a *Mycobacterium tuberculosis* beta-ketoacyl ACP synthase by isoniazid, Science (Wash.) vol. 280, No. 5369, pp. 1607-1610, USA (Abstract).
Koukilia-Kaehkoelae et al., *Mycobacterium branderi* sp. nov., a new potential human pathogen, Int. J. Syst. Bacteriol., vol. 45, No. 3, pp. 549-553, (1995),Finland (Abstract).
Davidson et al., Efficacy of over-the-counter nutritional supplements, Curr Atheroscler Rep pp. 15-21 (2003) USA (Abstract).
De Jong, Tobacco Leaf Protein: I. An evaluation of the use of putative chemical growth, Beitrage zur Tabakforschung Int., vol. 15, No. 1, pp. 33-42 (1991), USA (Abstract).
Re et al., Effects of some natural extracts on the acetylcholine release at the mouse neuromuscular junction, Pharmacol Res, vol. 39, pp. 239-245 (1999), Italy (Abstract).
Vasanth et al., Phytochemical study of *Leonotis nepetaefolia* RBr., Indian Drugs 26(3) pp. 127-128 (1988), India (Abstract).
Sugihara et al., Studies on intestinal lymphatic absorption of drugs, II. Glyceride prodrugs for, Journal of Pharmacobio-Dynamics 11(8), pp. 555-562 (1988) Japan (Abstract).
Harvey, D.J., Pyridine-containing derivatives for the structural elucidation of the alkyl chains, Spectroscopy 8(1-6) pp. 211-244 (1990) Netherlands (Abstract).
Iup et al., Results of the multicenter controlled study of the hypolipidemic drug polycosanol in Russia, Ter Arkh. 2000;72(12): pp. 7-10 (Abstract).
Kabir et al., Biodistribution and metabolism of orally administered octacosanol in rats, Ann Nutr Metab. 1993;37(1): pp. 33-38 (Abstract).
Liu et al., Active constituents lowering blood-lipid in beeswax, Zhongguo Zhong Yao Za Zhi. Sep. 1996;21(9): pp. 553-554 (Abstract).
Varady et al., Role of policosanols in the prevention and treatment of cardiovascular disease, Nutr Rev. Nov. 2003;61(11): pp. 376-383 (Abstract).
Pieper, J.A., Overview of niacin formulations: differences in pharmacokinetics, efficacy, Am J. Health Syst Pharm. Jul. 1, 2003;60(13 Suppl 2): S9-14; quiz S25 (Abstract).
Malik et al., Niacins, lipids, and heart disease, Curr Cardio Rep. Nov. 2003;5(6) 470-6 (Abstract).

(Continued)

*Primary Examiner*—Charanjit S Aulakh
(74) *Attorney, Agent, or Firm*—Oyen Wiggs Green & Mutala LLP

(57) ABSTRACT

This application pertains to compounds comprising unbranched long chain aliphatic alcohols linked to a heterocyclic carboxylic acid moiety by means of an ester or ether linkage. The aliphatic alcohols may include aliphatic alcohols present in polycosanol, such as octacosanol. The heterocyclic carboxylic acid moieties include a 5-membered ring, a 6-membered ring, or a bicyclic ring. In one embodiment, the compounds of the invention include 1-octacosanyl nicotinate and salts thereof. The invention includes prodrugs, pharmaceutically acceptable salts, and pharmaceutical compositions of the compounds, and methods of making and using the compounds.

3 Claims, No Drawings

OTHER PUBLICATIONS

NHLB1-CHD Cholesterol Lowering Medicines—Nicotinic Acid—pp. 1-2; http://www.nhlbi.nih.gov/chd/meds3.htm , May 12, 2004.

Policosanol, The Hoffman Center, (New York) http://www.drhoffman.com/policosanol , Feb. 1, 2004.

Medications for Lowering Your Cholesterol, http://www.lifeclinic.com/focus/cholesterol/Nicotinic_acid.asp , Feb. 1, 2004.

Cabrera, L. et al., Stability Studies of Tablets Containing 5 and 10 MG of Policosanol as Active Principle, Centro Nacional de Investigaciones Clientificas, Cuba (Abstract) , 2002.

Uribarri, E. et al., Physico-Mechanical Charcterization of DO03, A Novel Hypocholesterolemic Drug, Laboratorios MedSol, Cuba (Abstract) , 2002.

Hargrove et al., Policosanol: Waxes make cholesterol wane, FASEB Journal, vol. 17, No. 4-5, Mar. 2003, (Abstract).

Shepherd, T. et al., Effects of environment on the composition of epicuticular wax from kale and swede, Phytochemistry, vol. 40(2) pp. 407-414 (1995), U.K. (Abstract).

Molina, V. et al., Synergistic effect of D-003 and aspirin on experimental thrombosis, Prostaglandins Leukotrienes and, vol. 68(5), pp. 305-310, (2003), Cuba (Abstract).

Noa, M. et al., Effect of D-003, a mixture of high molecular, on CL4C-induced liver acute injury in rats, Drugs under Exp, vol. 28(5) pp. 177-183 (2002), Cuba (Abstract).

Mas, Rosa et al., Dose-dependent cholesterol-lowering effects of D-003, Current Therapeutic Research, vol. 61(7), pp. 460-468 (2000), Cuba (Abstract).

Molina, V. et al., D-003, a potential antithrombotic compound isolated from sugar cane wax, Prostaglandinds, Leukotrienes, vol. 67(1), pp. 19-24, (2002), UK (Abstract).

Gever, J.R. et al., Rice field surface microlayers: collection, composition and pesticide enrichment, Environmental Toxicol, vol. 15(10) pp. 1676-1682, (1996), USA (Abstract).

Lal, B. et al., Mineralization of Y super(14)C octacosane by Acinetobacter calcoacet S30, Can. J. Microbiol./rev. Can.., vol. 42(12), pp. 1225-1231, (1996), CA (Abstract).

Demchenko, A.V. et al., Synthesis and biological evaluation of Rhizobium sin-1 lipid A derivatives, J. Am. Chem. Soc., vol. 125(20), pp. 6103-6112, (2003), USA (Abstract).

Rodriguez, M.D. et al., Lack of developmental toxicity of D-003: a mixture of long-chain fatty acids in rats, Food Chem Toxicol, vol. 41, pp. 89-93, (2003), U.K. (Abstract).

Menendez, R. et al., Inhibition of rat lipoprotein lipid peroxidation by the oral administration of D003, Can J. Physiol. Pharmacol, vol. 80, pp. 13-21, (2002), CA (Abstract).

Menendez, R. et al., Inhibition of cholesterol biosynthesis in cultured fibroblasts by D003, Pharmacol Res., vol. 44, pp. 299-304, (2001), U.K. (Abstract).

Gamez, R. et al., Preliminary evaluation of the cytotoxic and genotoxic potential of D-003, Teratog Carcinog Mutagen, vol. 22, pp. 175-181, (2002), USA (Abstract).

Molina, V. et al., Antiplatelet and antithrombotic effect of D-003, Pharmacol Res., vol. 42, pp. 137-143, (2000) U.K. (Abstract).

McNevin, J.P. et al., Isolation and characterization of eceriferum (cer) mutants induced by T-DNA, Genome, vol. 36, No. 3, pp. 610-618, CA (Abstract) , 1993.

Kato, S. Karino et al., Octacosanol affects lipid metabolism in rats fed on high-fat diet, British Journal of Nutrition, 73, 433-441, (1995) UK.

Taconic Animal Models, Apoe (ApoE) Targeted Mutation Mice, http://www. taconic.com/anmodels/apos.htm , May 1998.

Shimura, S. et al., Studies on the effect of octacosanol on motor endurance in mice, Nutrition Reports International, 36(5), pp. 1029-1038 (1987) (Abstract).

Gouni-Berthold, I. et al., Policosanol: Clinical pharmacology and therapeutic significance of a new lipid-lowering agent, American Heart Journal 143(2), pp. 356-365 (1987).

Hernandez, F. et al., Effect of policosanol on serum lipids and lipoproteins in healthy volunteers, Current Therapeutic Research, 51, pp. 558-567 (1992).

Aneiros, E. et al., Effect of policosanol in lowering cholesterol levels in patients with type II hypercholesterolemia, Current Therapeutic Research, 56(2), pp. 176-182 (1995).

Pons, P. et al., Effects of success of dose increases of policosanol on the lipid profile of patients with type II, Int. Jour. of Clin Pharm. Res. 14(1), pp. 27-33 (1994).

Canetti, M. et al., One-year study of the effect of policosanol on lipid profile in patients with type II hypercholesterolemia, Advances in Therapy 12(4), pp. 245-254 (1995).

Delourdes, A. et al., Cholesterol-lowering effects of policosanol in rabbits, Biological Research, 27(3-4), pp. 205-208 (1994).

Wang, Y. et al., Effects of policosanols and phytosterols on lipid levels and cholesterol biosynthesis in hamsters, Lipids, 38(2), pp. 165-170 (2003).

Menendez, R. et al., Cholesterol-lowering effect of policosanol on rabbits with hypercholerterolaemia induced, British Journal of Nutrition, 77(1), pp. 923-932 (1997).

Canetti, M. et al., A Two-Year Study On The Efficacy And Tolerability Of Policosanol In Patients With Type II, Int. Jour. of Clin Pharm. Res. 14(4), pp. 159-165 (1995).

Cabrera, L. et al., Study of the stability of tablets containing 10 mg of policosanol as active principle, Bollettino chimico farmaceutico, 2002, 141(3):223-9. (Abstract).

Cabrera, L. et al., Stability studies of tablets containing 5 mg of policosanol, Bollettino chimico farmaceutico, 2003; 142 (7):227-84. (Abstract).

Uribarri, E. et al., Physico-mechanical characterization of policosanol, a novel hypocholesterolemic drug, Drug development and industrial pharmacy, 2002; 28(1):89-93. (Abstract).

* cited by examiner

LONG CHAIN ALIPHATIC ALCOHOL DERIVATIVES AND METHODS OF MAKING AND USING SAME

BACKGROUND

Polycosanol is a mixture of long chain alcohols that can be isolated from a number of plants, including sugar cane. Polycosanol has been found to reduce blood cholesterol levels by reducing levels of low-density lipoproteins (LDLs), which are associated with an increase in the risk of cardiovascular disease. Polycosanol also raises levels of high-density lipoproteins (HDLs), which are associated with a decrease in the risk of cardiovascular disease. Further, polycosanol has also been found to prevent the formation of arterial wall lesions, and to act as an anti-coagulant (Varada et al., Nutr. Rev. November 2003: 61(11):375-83) and prevent platelet aggregation (Taylor et al., Nutrition, Vol. 19, 192-195, 2003). Preventing platelet aggregation and blood coagulation may help reduce incidences of stroke and blood clotting. Polycosanol may also enhance athletic performance and may inhibit stomach ulcer formation aggregation (Taylor et al., Nutrition, Vol. 19, 192-195, 2003).

One of the main components of polycosanol is the long chain aliphatic alcohol octacosanol. Other aliphatic alcohols, which may be present in polycosanol include hexacosanol, triacontanol, eicosanol, tetracosanol, nonacosanol, dotriacontanol, tetratriacontanol, and heptacosanol.

Nicotinic acid, also known as niacin, is a water-soluble B vitamin. Nicotinic acid is a heterocyclic carboxylic acid. Nicotinic acid can also lower LDL levels and raise HDL levels. In addition, nicotinic acid lowers triglyceride levels, which can also help reduce the risk of heart disease. However, serious side effects are associated with the use of nicotinic acid including hot flushes, gastrointestinal disorders, hepatotixicity, gout, and blood sugar level elevation (Am. J. Health Syst Pharm. 2003 Jul. 1; 60(13 Suppl 2):S9-14).

Many aliphatic alcohol derivatives are described in the prior art. For example, Bertelsen et al. have described structural elucidation of alkyl-branched chain aliphatic alcohols by mass spectrometry of their respective alkyl nicotinate and picolinyl carboxylate derivatives.[1] The Bertelsen et al. paper describes transformation of aliphatic alcohols into alkyl nicotinates by condensation with nicotinyl chloride hydrochloride. All of the esters obtained were alkyl-branched chain alkyl nicotinates. No unbranched chain alkyl nicotinates were characterized. Moreover, Bertelsen et al. did not describe possible use of the esters for reducing risk of cardiovascular disease, such as by lowering serum cholesterol levels.

There is a need for new aliphatic alcohol derivatives having the beneficial effects of polycosanol and nicotinic acid.

SUMMARY OF INVENTION

The invention pertains to compounds comprising aliphatic alcohols linked to heterocyclic carboxylic acid moieties. The linkages can be ester or ether linkages. The aliphatic alcohols may include alcohols comprising polycosanol, such as octacosanol.

The aliphatic alcohols can comprise unbranched aliphatic alcohols having 20 to 34 carbons, such as aliphatic alcohols derived from polycosanol. Such alcohols include octacosanol, hexacosanol, triacontanol, eicosanol, tetracosanol, nonacosanol, dotriacontanol, tetratriacontanol, and heptacosanol.

The heterocyclic carboxylic acid moieties include a 5-membered ring, a 6-membered ring, or a bicyclic ring. The bicyclic ring can comprise 5-membered rings, 6-membered rings, or both. The ring may include a nitrogen atom. In some embodiments, the heterocyclic carboxylic acid moiety is nicotinic acid. In one embodiment, the compounds include 1-octacosanyl nicotinate and salts thereof.

The invention also includes prodrugs of the compounds, pharmaceutically acceptable salts of the compounds, and pharmaceutical compositions comprising the compounds of the invention, pharmaceutically acceptable salts of the compounds, and prodrugs of the compounds.

The invention also pertains to methods of making the compounds and methods of reducing blood cholesterol levels and blood triglyceride levels, methods of preventing the formation of arterial wall lesions, methods of preventing platelet aggregation, methods of enhancing athletic performance, methods of inhibiting stomach ulcer formation, and methods of treating any condition responsive to polycosanol or nicotinic acid therapy.

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

This invention pertains to aliphatic alcohol derivatives and methods of making and using same. The compounds of the invention comprise aliphatic alcohols linked to a heterocyclic carboxylic acid moiety by means of an ester or ether linkage.

The aliphatic alcohols can comprise any unbranched aliphatic alcohol, such as an aliphatic alcohol found in polycosanol. In some embodiments the aliphatic alcohols have between 20 and 34 carbons and include octacosanol, hexacosanol, triacontanol, eicosanol, tetracosanol, nonacosanol, dotriacontanol, tetratriacontanol, and heptacosanol. In one embodiment, the aliphatic alcohol comprises octacosanol.

The heterocyclic carboxylic acid moieties can comprise a 5-membered heterocyclic ring, a 6-membered heterocyclic ring, or a bicyclic heterocyclic ring. The bicyclic ring can comprise either two 5-membered rings, two 6-membered rings, or one 5-membered ring and one 6-membered ring. The heterocyclic ring of the heterocyclic carboxylic acid moieties may also comprise a nitrogen atom. The heterocyclic carboxylic acid moieties can be derived from nicotinic acid, indole carboxylic acid, dihydroindole carboxylic acid, quinoline carboxylic acid, dihydroquinoline carboxylic acid, tetrahydroquinoline carboxylic acid, isoquinoline carboxylic acid, pyridine carboxylic acid, piperidine carboxylic acid, methylindole carboxylic acid, methyldihydroindole carboxylic acid, methylquinoline carboxylic acid, methyldihydroquinoline carboxylic acid, methyltetrahydroquinoline carboxylic acid, methylisoquinoline carboxylic acid, pyrrolidine carboxylic acid, furan carboxylic acid, tetrahydrofuran carboxylic acid, benzofuran carboxylic acid, thiophene carboxylic acid, tetrahydrothiophene carboxylic acid, benzothiophene carboxylic acid, methylbenzothiophene carboxylic acid, methylpyridine carboxylic acid, methylpiperidine carboxylic acid, methylpyrrolidine carboxylic acid, methylfuran carboxylic acid, methyltetrahydrofuran carboxylic acid, methylbenzofuran carboxylic acid, methylthiophene carboxylic acid, methyltetrahydrothiophene carboxylic acid, and dimethylbenzothiophene carboxylic acid. In one embodiment, the heterocyclic carboxylic acid moiety is derived from nicotinic acid.

The aliphatic alcohol and the heterocyclic carboxylic acid moiety can be linked through ester or ether linkages. In one embodiment, the compound of the invention is the ester octacosanyl nicotinate having the formula:

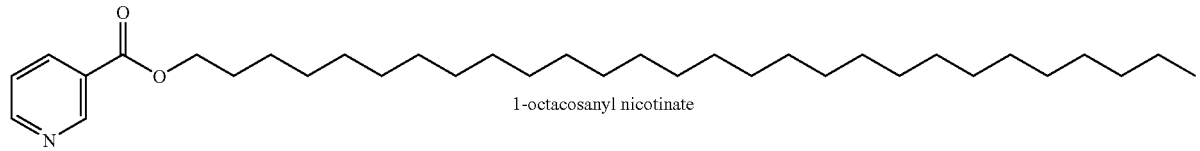

1-octacosanyl nicotinate

In other embodiments, the compounds of the invention have the following formulae:

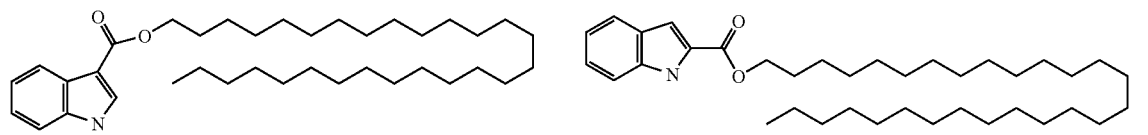

Octacosanyl indole carboxylate

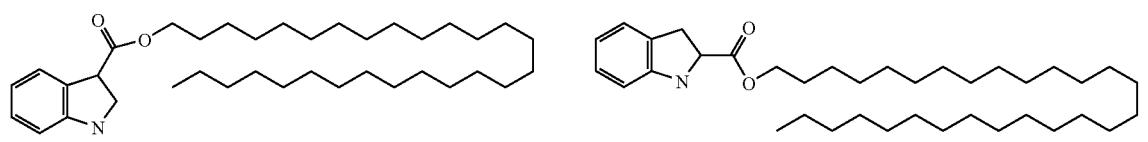

Octacosanyl dihydroindole carboxylate

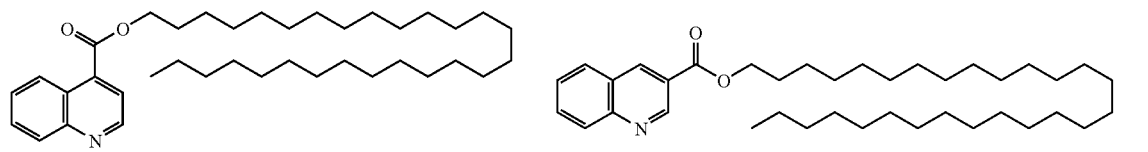

Octacosanyl quinoline carboxylate

Octacosanyl dihydroquinoline carboxylate

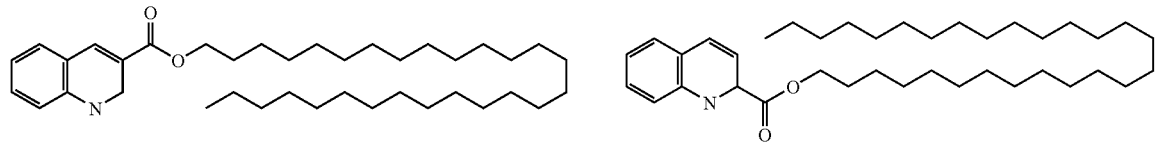

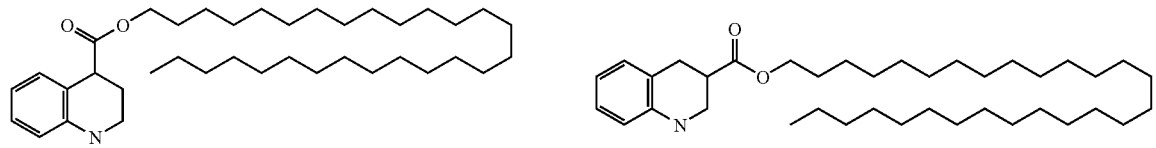

Octacosanyl tetrahydroquinoline carboxylate

-continued
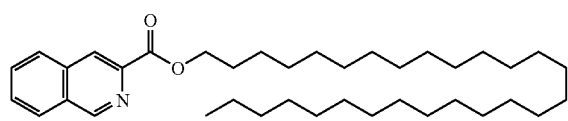
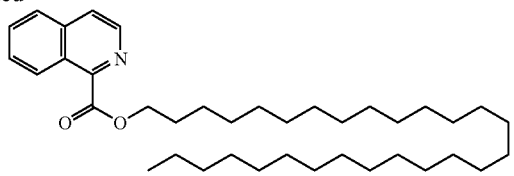
Octacosanyl isoquinoline carboxylate
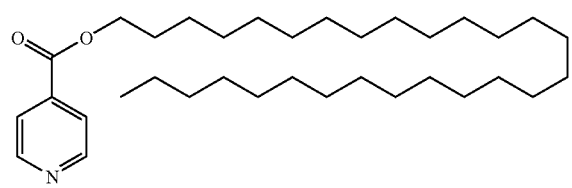
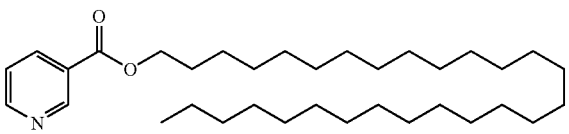
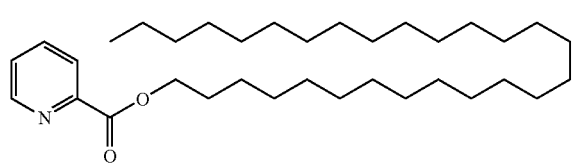
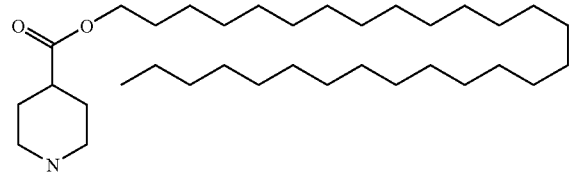
Octacosanyl pyridine carboxylate
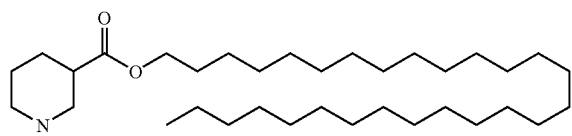
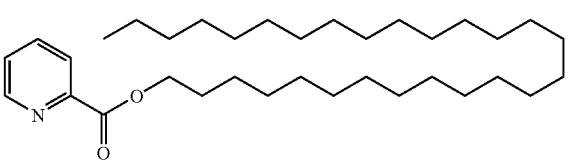
Octacosanyl piperidine carboxylate
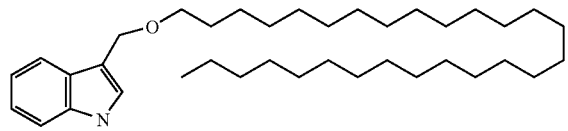
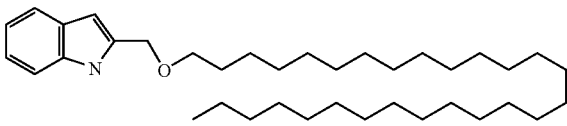
Octacosanoxymethylindole
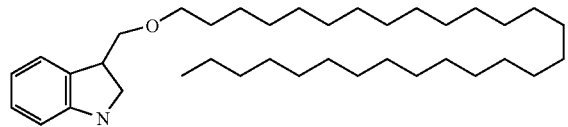
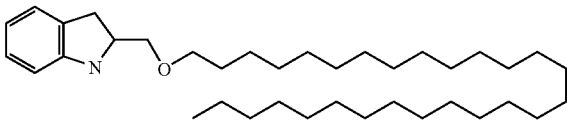
Octacosanoxymethyldihydroindole
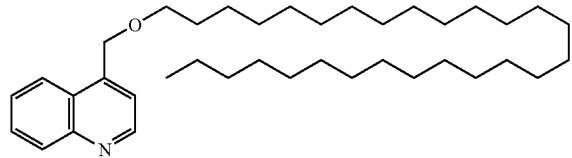
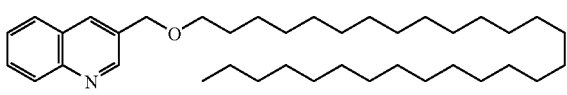
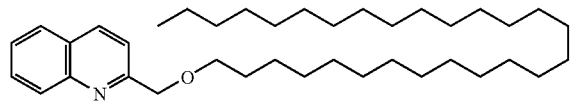
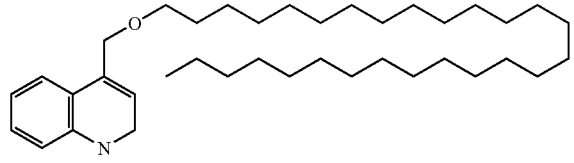
Octacosanoxymethylquinoline
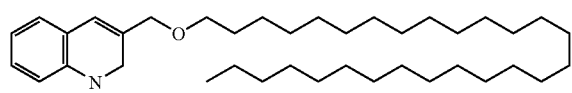
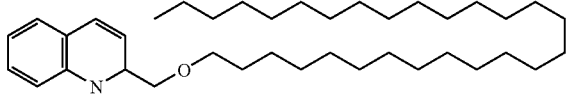
Octacosanoxymethyldihydroquinoline -continued
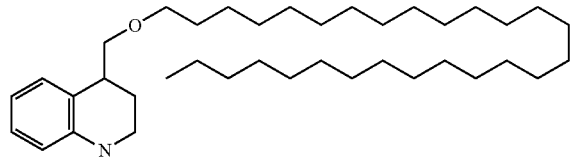
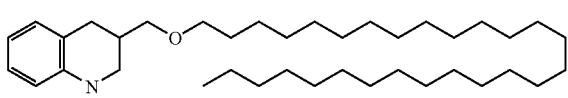
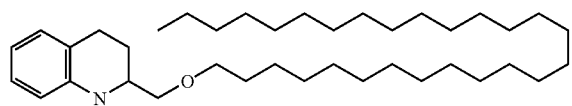
Octacosanoxymethyletrahydroquinoline
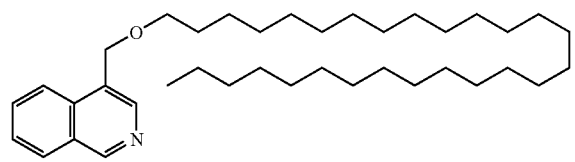
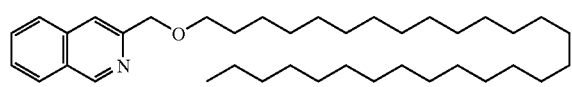
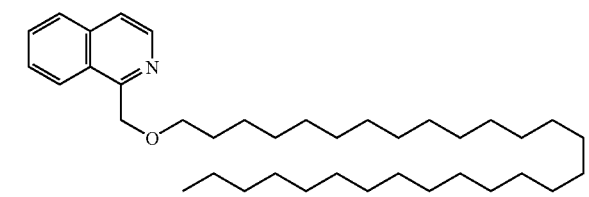
Octacosanoxymethylisoquinoline
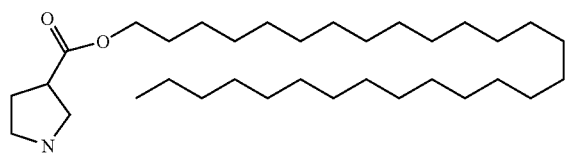
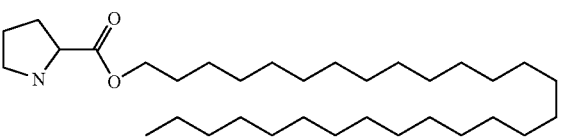
Octacosanyl pyrrolidine carboxylate
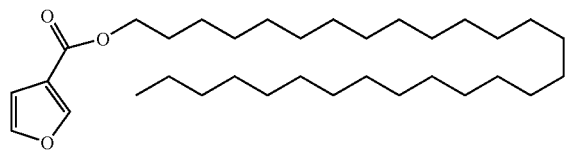
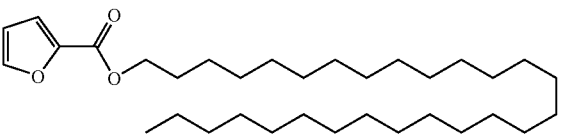
Octacosanyl furan carboxylate
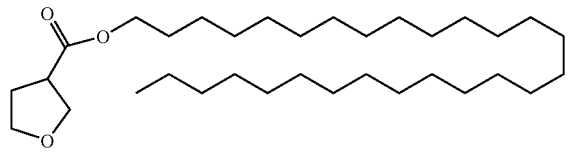
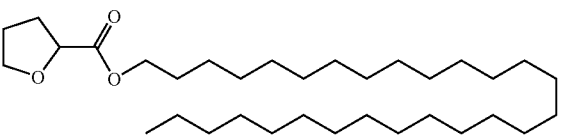
Octacosanyl tetrahydrofuran carboxylate
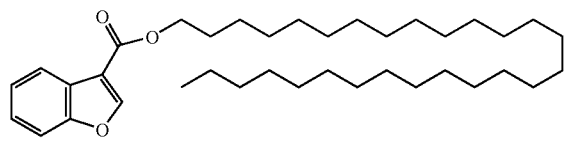
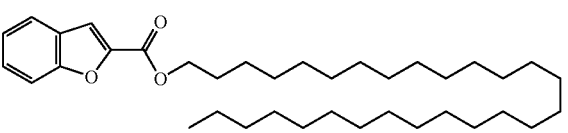
Octacosanyl benzofuran carboxylate
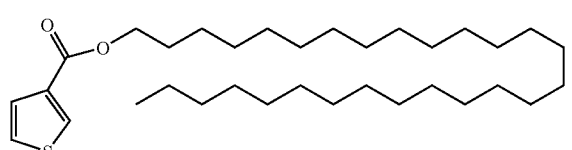
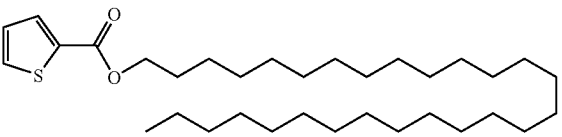
Octacosanyl thiophene carboxylate
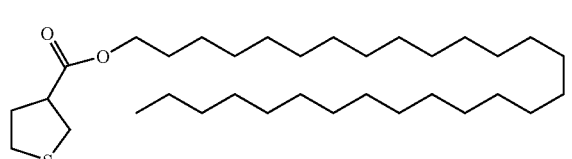
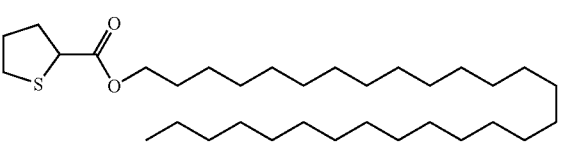
Octacosanyl tetrahydrothiophene carboxylate -continued
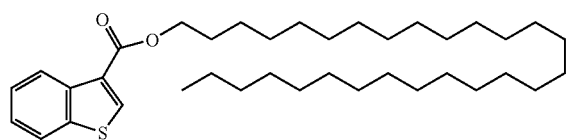
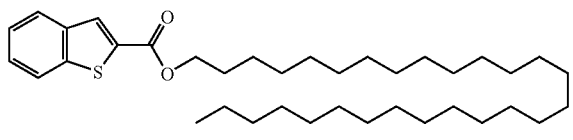
Octacosanyl benzothiophene carboxylate
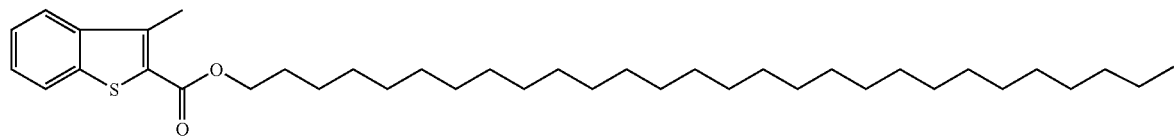
2-octacosanyl-3-methylbenzothiophene carboxylate
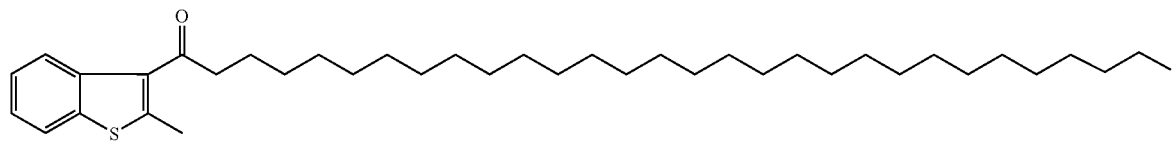
3-octacosanyl-2-methylbenzothiophene carboxylate
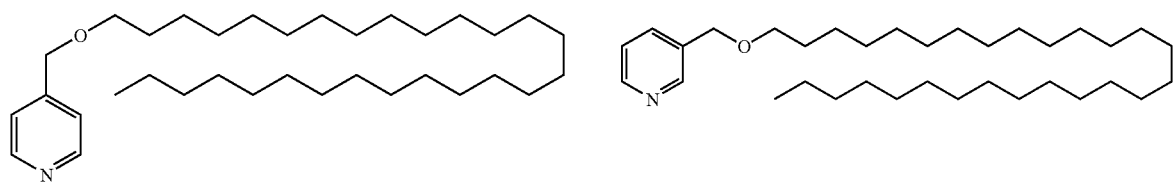
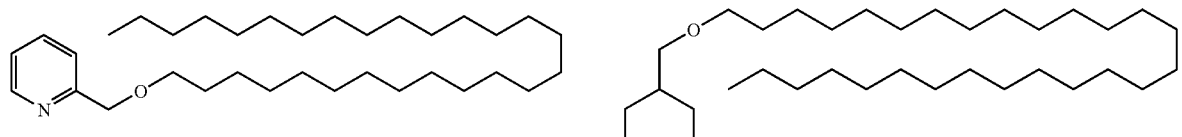
Octacosanoxymethylpyridine
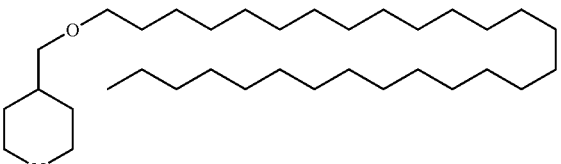
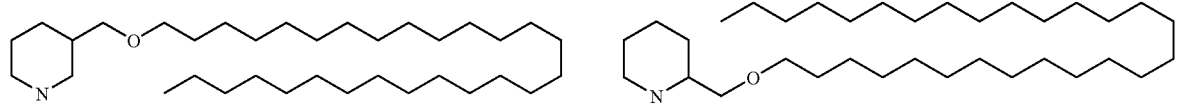
Octacosanoxymethylpiperidine
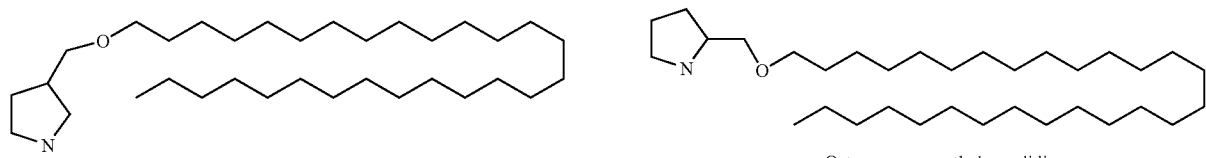
Octacosanoxymethylpyrrolidine
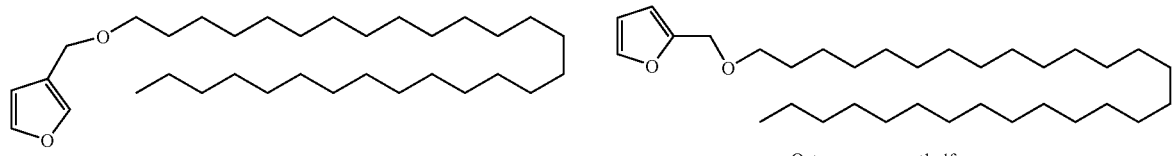
Octacosanoxymethylfuran
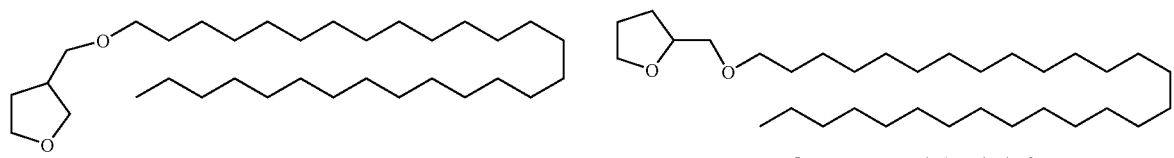
Octacosanoxymethyltetrahydrofuran -continued

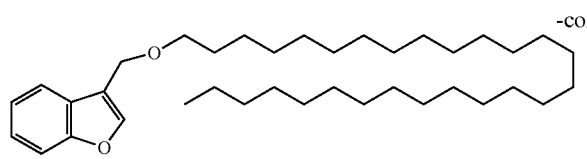

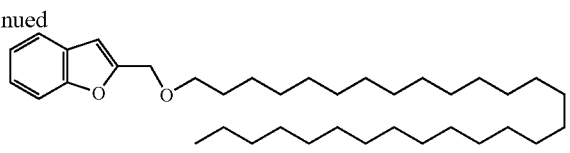

Octacosanoxymethylbenzofuran

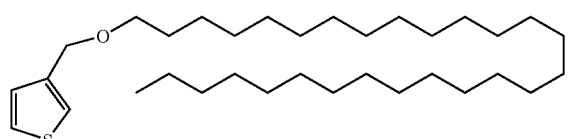

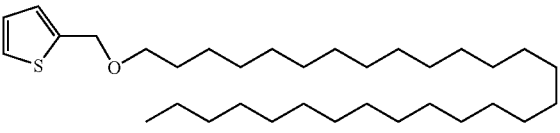

Octacosanoxymethylthiophene

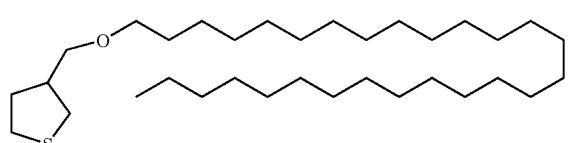

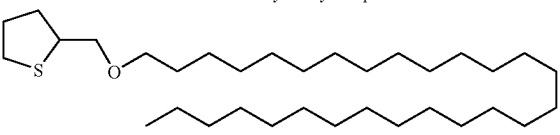

Octacosanoxymethyltetrahydrothiophene

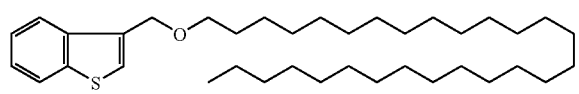

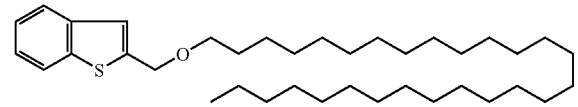

Octacosanoxymethylbenzothiophene

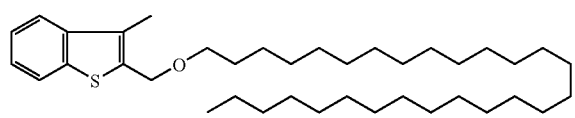

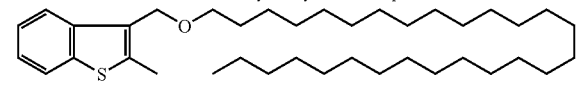

2-methyloctacosanoxy-3-methylbenzothiophene 3-methyloctacosanoxy-2-methylbenzothiophene The invention also includes pharmaceutically acceptable salts of the above compounds. Such salts include hydrochlorides, chlorides, fluorides, phosphates, sulphates, acetates, nitrates, and other acceptable salts.

The invention also pertains to prodrugs transformable into the compounds of the invention. Such prodrugs include salts of the compounds of the invention. In one embodiment, the salt is a chloride salt.

The invention also pertains to pharmaceutical compositions comprising the compounds of the invention, pharmaceutically acceptable salts of the compounds, and prodrugs transformable into the compounds. The pharmaceutical compositions comprise a pharmaceutically effective amount of one or more of the compounds, salts of the compounds or prodrugs of the compounds and a pharmaceutically effective carrier.

The invention also pertains to methods of reducing blood cholesterol levels and blood triglyceride levels, methods of preventing the formation of arterial wall lesions, methods of preventing platelet aggregation, methods of enhancing athletic performance, methods of inhibiting stomach ulcer formation, and methods of treating any condition responsive to polycosanol or nicotinic acid therapy using the compounds of the invention, pharmaceutically acceptable salts of the compounds, prodrugs of the compounds, or pharmaceutical compositions containing the compounds, pharmaceutically acceptable salts of the compounds, or prodrugs of the compounds. The compounds of the invention can be used to treat any condition responsive to treatment with polycosanol or nicotinic acid by administering the compounds of the invention, the salts of the compounds, the prodrugs of the compounds, or any pharmaceutical composition containing the compounds, salts of the compounds, or prodrugs of the compounds and a pharmaceutically acceptable carrier to a patient in need of treatment.

The invention also pertains to methods of making the compounds of the invention. In one embodiment, the method includes steps for producing octocosanol and for producing the compound of the invention in the form of an ester.

The method for producing octacosanol comprises:
a) Extracting wax from plants using ethanol;
b) Saponifying and hydrolyzing the wax using $Ca(OH)_2$, KOH, NaOH, or any other suitable base;
c) Filtering away insoluble precipitate;
d) Cooling the filtrate to 5° C. to −20° C. for 24 hours or more to produce a mixture of long chain fatty alcohols;
e) Vacuum distilling the residual alcohol mixture to separate individual alcohols;
f) Optionally repeating the vacuum distilling step;
g) Recrystalizing octacosanol from the separate individual alcohols; and
h) Oven drying octacosanol to remove residual solvent.

In one embodiment of the invention, the wax is saponified with $Ca(OH)_2$ and the filtrate is cooled to 0° C. to 5° C.

The method of producing the compound of the invention comprises:
a) converting a heterocyclic carboxylic acid into a salt; and
b) reacting the salt of the heterocyclic carboxylic acid with an aliphatic alcohol.

In one embodiment of the invention, the method comprises steps for making 1-octacosanyl nicotinate and salts thereof, said method comprising:

a) conversion of nicotinic acid to nicotinyl chloride using thionyl chloride or phosphorus oxychloride; and
b) reaction of nicotinyl chloride with octacosanol to yield 1-octacosanyl nicotinate hydrochloride.

The reaction can take place in the presence of solvents such as ethers, including diethyl ether, tetrahydrofuran, and dioxane, or in the presence of chlorinated solvents, including chloroform, dichloromethane, and carbon tetrachloride, or any other suitable solvent.

The salt 1-octacosanyl nicotinate hydrochloride can be further reacted with $NaHCO_3$ to obtain octacosanyl nicotinate ester.

In a further option, 1-octacosanyl nicotinate hydrochloride can be obtained from octacosanyl nicotinate ester by reacting octacosanyl nicotinate ester with HCl to obtain octacosanyl nicotinate hydrochloride (see Scheme 1).

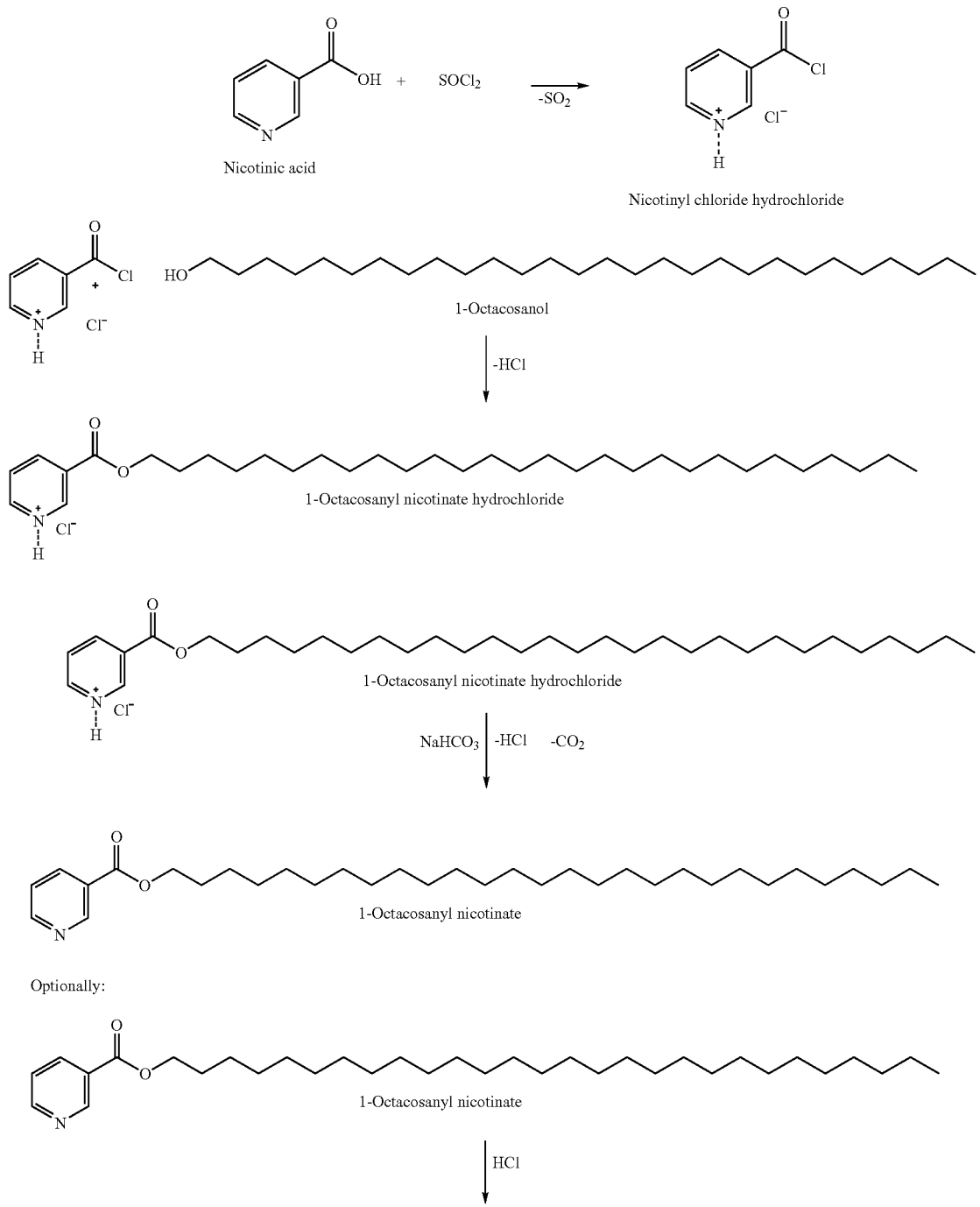

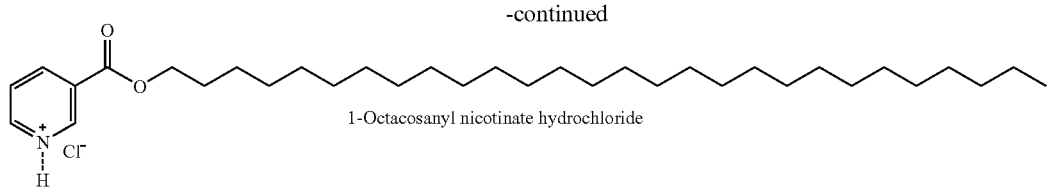

1-Octacosanyl nicotinate hydrochloride

EXAMPLES

The following examples illustrate embodiments of the invention and are not intended to limit the scope of the invention.

1. Octacosanol Extraction Method

Wax extract can be produced from sugarcane wax or other plant materials. Extraction was carried out by extracting of 100 kg sugarcane wax with 500 L of food grade ethanol. Saponification and hydrolysis was achieved using 10% Ca(OH)$_2$ solution at 60-100° C. for 2-10 hours. The insoluble precipitate was filtered off and the filtrate was cooled at 0-5° C. for 24 hours to produce a mixture of long chain fatty alcohols. The residual alcohol mixture was vacuum distilled at 180-250° C. to separate the individual alcohols. The distillation procedure was repeated to obtain 95% pure C28 alcohol (Octacosanol). The product was recrystalized twice to increase the purity to more than 98% and oven dried to remove the residual solvent. The analytical results have illustrated the following long chain fatty alcohol compositions:

C24 Alcohol 0-1.0%
C26 Alcohol 0.5-2.0%
C27 Alcohol 0.3-1.0%
C28 Alcohol 90-98% or greater
C29 Alcohol 0.3-1.0%
C30 Alcohol 0.6-4%
C32 Alcohol 0.3-1.0%

2. Synthesis of 1-octacosanyl nicotinate hydrochloride

Commercial SOCl$_2$ (>99.5) and nicotinic acid (>99.5) were used without any further purification. To a three-necked flask was added nicotinic acid (16.9 g, 0.137 mol) under dry nitrogen atmosphere, and commercial SOCl$_2$ (50 ml, 0.685 mol) was added dropwise. The mixture was heated to reflux for 3 hours and SOCl$_2$ was evaporated under dry nitrogen atmosphere. After cooling to room temperature, 1-octacosanol (23.45 g, 0.057 mol) and CHCl$_3$ (300 ml, dried anhydrous Na$_2$SO$_4$) were added to the nicotinic chloride and the mixture was heated to reflux for 4 hours. After cooling to room temperature overnight, the mixture was filtered under reduced pressure. The precipitate was dissolved in warm CHCl$_3$ (800 ml) and then saturated NaHCO$_3$ (100 ml) was added slowly. After stirring at room temperature for 1 hour, the organic layer was separated, washed with deionized water, brine and then dried over anhydrous Na$_2$SO$_4$. After the removal of the organic solvent, the residue was dissolved in warm CHCl$_3$ (150 ml) and concentrated HCl (5 ml) was added with vigorous stirring for 30 minutes. The mixture was filtered under reduced pressure and the precipitate was washed with deoinized water, 95% EtOH, to obtain the product octacosanyl nicotinate hydrochloride (28.4 g, 90.3% yield, mp: 58-60° C.) as a pale yellow solid, and then recrystallized with CHCl$_3$ to give 24.3 g of octacosanyl nicotinate hydrochloride in yield 77.3%, mp: 74-75° C.

3. Synthesis of 1-octacosanyl nicotinate

To a solution of 1-octacosanyl nicotinate hydrochloride in warm CHCl$_3$ was added saturated NaHCO$_3$ slowly. The aqueous layer was kept basic and the mixture was stirred for 1 hour at room temperature. The organic layer was then separated, washed with deionized water, brine and dried over anhydrous Na$_2$SO$_4$. After the removal of the organic solvent, the residue was crystallized with CHCl$_3$ to give 1-octacosanyl nicotinate as a pale yellow waxy solid, mp: 65-70° C.

4. Spectroscopic Analysis $^1$H spectra were recorded in CDCl$_3$ on a VARIAN MERCURY-300. The LCMS data were recorded using a Waters ZQ10 instrument. The purification of the final products (1-octacosanyl nicotinate and 1-octacosanol nicotinate hydrochloride) were all 100.0 detected by HPLC on a HP1100 instrument.

1-Octacosanyl nicotinate hydrochloride:

$^1$HNMR(CDCL$_3$, 300 MHz): 0.87 (3H, t, J=6 Hz, —CH3), 1.24-1.80 (52H, m, —(CH2)26-), 4.35 (2H, t, J=6.6 Hz, —OCH2-), 7.26 (solvent), 7.39 ($^1$H, dd, J1=4.2, J2=7.8, Ar—H5), 8.30 ($^1$H, d, J=7.8, Ar—H4), 8.77 ($^1$H, d, J=4.2, Ar—H6), 9.23 ($^1$H, s, Ar—H2). EI-MS: 515 (85, M+), 486 (10, M−29), 124 (100).

LCMS of 1-octacosanyl nicotinate ester
Solvent: tetrahydrofuran—water=9:1.
Ionization—positive
Calculated mass for molecular ion [M.H]+(C34H62NO2)= 516.478055
Determined mass=517.09
LCMS of octacosanoyl nicotinate hydrochloride
Solvent: tetrahydrofuran-water=9:1.
Ionization—negative
Calculated mass for molecular ion [M-H]—(C34H61ClNO2)=550.439083.
Determined mass=551.05.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A method of synthesizing 1-octacosanyl nicotinate comprising the steps of:
   a) Converting nicotinic acid to nicotinyl chloride using thionyl chloride or phosphorus oxychloride;
   b) Reacting nicotinyl chloride with octacosanol to produce 1-octacosanyl nicotinate hydrochloride; and
   c) Reacting 1-octacosanyl nicotinate hydrochloride with NaHCO$_3$ to obtain octacosanyl nicotinate.

2. A method of synthesizing 1-octacosanyl nicotinate hydrochloride comprising the steps of:
   a) Converting nicotinic acid to nicotinyl chloride using thionyl chloride or phosphorus oxychloride; and
   b) Reacting nicotinyl chloride with octacosanol to produce 1-octacosanyl nicotinate hydrochloride.

3. A method of synthesizing a salt of 1-octacosanyl nicotinate comprising the steps of reacting octacosanyl nicotinate with HCl to obtain octacosanyl nicotinate hydrochloride.

* * * * *